United States Patent [19]

Kalnberz

[11] 4,033,340

[45] July 5, 1977

[54] SURGICAL COMPRESSION-DISTRACTION INSTRUMENT

[76] Inventor: Viktor Konstantinovich Kalnberz, ulitsa Stendera, 13, kv. 2, Riga, U.S.S.R.

[22] Filed: Dec. 9, 1974

[21] Appl. No.: 531,192

[30] Foreign Application Priority Data

Dec. 14, 1973 U.S.S.R. .......................... 1973053

[52] U.S. Cl. ............................................. 128/92 A
[51] Int. Cl.² .......................................... A61F 5/04
[58] Field of Search ............. 128/92 A, 92 R, 92 B, 128/83, 84

[56] References Cited

UNITED STATES PATENTS

| | | | |
|---|---|---|---|
| 1,982,140 | 11/1934 | Martin | 128/84 R |
| 2,055,024 | 9/1936 | Bittner, Jr. | 128/92 A |
| 2,056,749 | 10/1936 | Thomas | 128/92 A |
| 2,687,720 | 8/1954 | Haboush | 128/84 R |
| 3,727,610 | 4/1973 | Riniker | 128/84 R |

*Primary Examiner*—John D. Yasko

[57] ABSTRACT

The surgical instrument is adapted to adjust the position of bone fragments of a limb. It has an outer ring with longitudinal connecting members and a smaller ring carrying clamps for needles fixed within the larger ring. A system of threaded studs enables the inner ring to move in any direction and turn within the outer ring. The inner ring can also be positioned in a plane turned by an angle with respect to the plane of the outer ring.

4 Claims, 4 Drawing Figures

SURGICAL COMPRESSION-DISTRACTION INSTRUMENT

The present invention relates to medical equipment and, in particular, to surgery; it is an improvement in or related to compression-distraction instruments widely employed for treating injuries and diseases of bones and joints.

It is known in the art to employ such a compression-distraction instrument, which comprises needles that can be passed through the broken-off bone fragments and secured in rings or half-rings. The rings are interconnected by longitudinal connecting members, and at least one of the rings is composed of two concentric members, an inner and an outer one. The inner ring carries needle clamps, while the outer ring is connected with the longitudinal members.

Such widely known compression-distraction instruments, designed by O. N. Gudushauri, G. A. Ilizarov, K. M. Sivash and others, are sufficiently effective in correcting lengthwise and angular dislocations of the bone fragments. The lengthwise dislocation of the fragments is readily corrected by removing or approximating the rings (or half-rings) of the instrument, whereas the angular dislocation of the fragments is dealt with by inclining the rings (or half-rings) of the instrument.

It is in cases of rotary dislocation of the fragments that difficulties arise. The special attachment provided in O. N. Gudushauri's instrument to cope with such cases has a limited utility, whereas G. A. Ilizarov's instrument envisages a very complex procedure for the rotation of the rings.

There also exists a compression-distraction instrument according to the U.S.S.R. Inventor's Certificate No. 367,858. This instrument, developed by M. I. Sinilo, S. D. Sarancha and A. G. Nadein, comprises a slotted support arch, a distal arch and a split ring, as well as coupling screws, needles and fastening members, the ring being connected with the support arch by means of threaded link studs arranged radially and tangentially with respect to the ring.

The above-described prior art instrument has the following disadvantages:
  the ring with the needles cannot be laterally displaced, making it impossible to correct lateral dislocations of the bone fragments;
  the ring has a limited degree of freedom in a rotary sense, so that rotary dislocations of the bone fragments cannot be fully corrected; nor can the instrument be employed for corrective surgery, e.g. derotational osteotomy;
  the design is too sophisticated; the instrument is difficult to install and adjust.

It is an object of the present invention to provide a surgical compression-distraction instrument capable of correcting not only longitudinal and angular but also rotary and lateral dislocations of bone fragments.

It is another object of the invention to provide a simple instrument for treating injuries and diseases of bones and joints.

It is a further object of the invention to provide a surgical compression-distraction instrument adapted to correct the orientation of an individual bone fragment in the course of treatment without dismantling the instrument.

These and other objects are attained by the provision of a surgical compression-distraction instrument for treating injuries and diseases of bones and joints, comprising needles that are adapted to be passed through the bone fragments and secured in rings which are interconnected by longitudinal connecting members, wherein at least one of the rings is composed of two concentric members, an inner member and an outer one, the inner member carrying needle clamps and the outer member being connected with the longitudinal members. In accordance with the present invention, the inner needle-carrying member is formed as a ring from which protrude outwardly radial rods fastened to the outer ring, connected with the longitudinal members of the instrument. There are also provided threaded attachments for fastening the radial rods of the inner ring to the outer ring anywhere along the rods and over a selected section along the circumference of the outer ring.

Owing to such a construction, the inner ring carrying the needles can be moved about in any direction within the outer ring, fixing it in a required position, which provides for an unhindered displacement of the affected bone fragment in the course of treatment of the affected joint.

The proposed surgical instrument is further characterized, in accordance with the invention, in that the outer member is preferably made up of two parallel rings mounted with the aid of spacers with a certain clearance therebetween, and the radial rods are formed as threaded stays which are displaced in the course of adjustments in the clearance and are fastened by means of nuts to the outer rings in a desired position.

The foregoing exemplary embodiment is one of the most successful versions of a compound ring for instrument of the type being described; it is particularly convenient for practical purposes.

In accordance with a further, optional feature of the present invention, the instrument is characterized in that the inner ring has a diameter 1.5 times less than that of the outer ring such a diameter ratio of the outer and inner rings is particularly convenient if the instrument is to be practicable and compact.

In accordance with yet another optional feature of the present invention, the inventive instrument is characterized in that the inner ring can be installed in a plane turned angularly relative to the plane of the outer ring, for which purpose the outer ring and the ends of the radial rods of the inner ring are provided with eyes for receiving threaded distance studs that can be secured by nuts in any desired position. This improvement gives the added possibility of withdrawing the inner ring with the needles and the bone fragment secured therein from the plane of the outer ring at a prescribed angle.

Thus, the inventive compound ring for compression-distraction instruments, for instance for the widely known instrument designed by G. A. Ilizarov, considerably expands the clinical potential of those instruments. With one or several rings of the instrument replaced by the proposed ring, all the necessary lateral, rotative and angular displacements of the bone fragments can be easily performed, requiring no slackening of the needle tautness, nor reduction in the degree of stretching or compression of the bone fragments. This feature may prove important in corrective osteotomy, for instance in cases of derotational osteotomy of the limbs.

The attachment is quite simple in design; it requires no special apparatus or tools to be installed. Since by its dimensions the novel ring corresponds to the standard rings, e.g. those which are used in G. A. Ilizarov's instrument, it can furthermore easily be replaced in the course of treatment, with the general arrangement of the instrument being unaffected.

The present invention will be further understood and its various advantages more fully appreciated from the following detailed description of an exemplary embodiment of the inventive instrument, taken in conjunction with the accompanying drawings, wherein.

Figure 4:
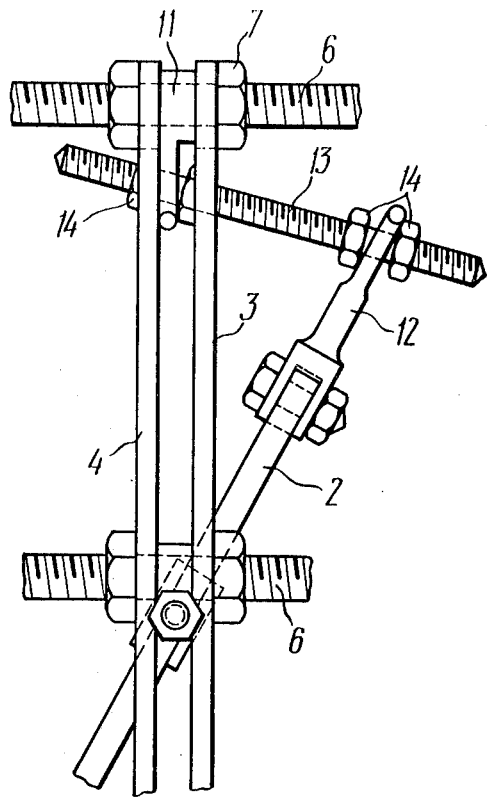
FIG. 4 shows in another partial view angular displacement of the inner ring with respect to the outer ring.

Referring now to the drawings, it will be seen that in a conventional manner the inventive surgical compression-distraction instrument has a compound ring that comprises an outer ring 1 (FIGS. 1, 2) with openings through which are passed rods 6 of the instrument and an inner ring 2, the diameter of the inner ring 2 being at least 1.5 times smaller than that of the outer ring 1. The outer ring is made up of two flat spaced-apart rings 3 and 4 (FIGS. 3, 4) with a spacer 5 in between. The rings 3 and 4 and the spacer 5 are mounted on the rods 6 of the compression-distraction instrument and secured by nuts 7.

Figure 1:
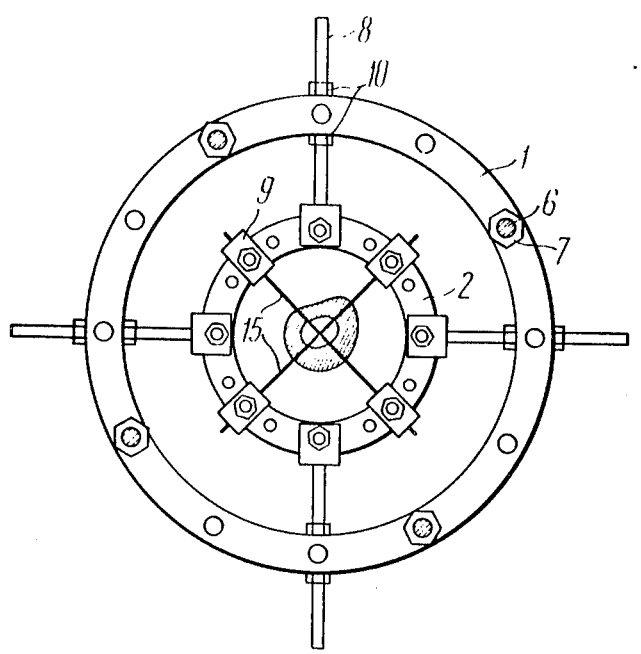
FIG. 1 is a general plan view of the inventive compression-distraction instrument including a compound ring.
Figure 2:
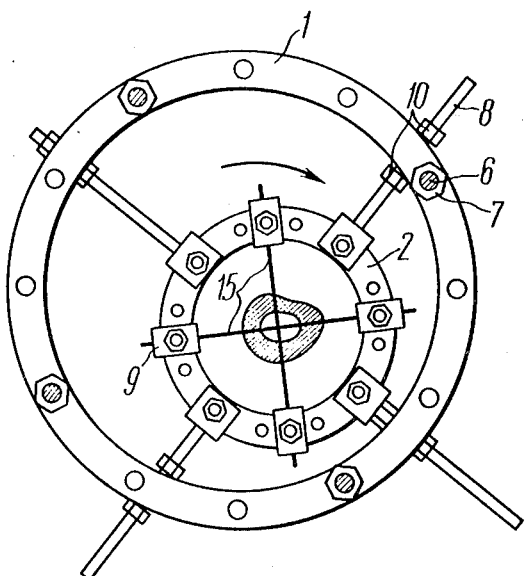
FIG. 2 illustrates in a similar plan view the way an inner ring is displaced relative to an outer ring of the instrument in the course of treatment.
Figure 3:
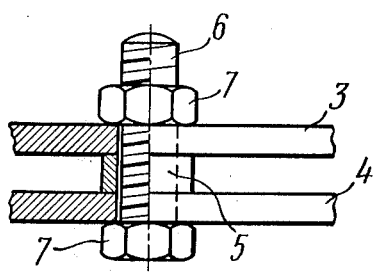
FIG. 3 shows in a partial view the outer ring mounted on rods forming part of the compression-distraction instrument.

The rings 3 and 4 may be assembled from half-rings. The inner ring 2 is composed of two half-rings and carries outwardly protruding threaded studs 8 (FIGS. 1, 2) and clamps 9 for immobilizing needles 15. FIGS. 1 and 2 schematically show a bone fragment, e.g. of a limb, through which the needles 15 can be passed in a conventional manner. The outer ends of the threaded studs 8 are disposed in a radial clearance or slot between the rings 3 of the outer ring 1 and 4 (FIGS. 3, 4), and, owing to the fact that the height of the spacer 5 is less than the diameter of the threaded latter, the ends of the studs 8 are free to move in the clearance. The ends of the threaded studs 8 are secured in the outer ring 1 (FIGS. 1, 2) by means of nuts 10.

In order to enable angular displacements of the bone fragments, one or two diametrically opposite spacers 5 may be replaced by spacers 11 (FIG. 4) having eyes, and one or two diametrically opposite threaded studs 8 may be replaced by brackets 12 with eyes. In such a case a screw stay 13 also having nuts 14 is installed therebetween. By adjusting the length of the screw stay 13, the inner ring 2 is enabled to execute angular displacements with respect to the outer ring 1.

The inventive compression-distraction instrument can be installed in the following way. Two needles 15 (FIGS. 1, 2) are preferably passed in a cruciform manner through the bone or fragment in the distal portion of the affected limb. The inner ring 2 is installed at the level of the needle passage. Using the special clamps 9, the needles 15 are tautened and secured to the inner ring 2. The ring 1 is assembled at the level of the fixed inner ring 2 in such a way that the threaded studs 8 of the inner ring 2 are disposed in the radial slots formed in the ring 1 between the rings 3 and 4 and fixed therein by the nuts 10.

The bone fragments can be laterally moved by displacing the respective threaded studs 8, which is achieved by turning the nuts 10. The bone fragments can be turned by rotating the threaded studs 8 in the radial clearance of the outer ring 1 with the nuts 10 loosened; subsequently they are fixed in a desired position.

The bone fragments can also be displaced angularly by installing the spacers 11 between the rings 3 and 4 (FIG. 4), mounting the brackets 12 on the inner ring 2, connecting them by means of the screw stays 13 with the nuts 14, and subsequently varying the length of the screw stays 13.

What is claimed is:

1. A surgical compression-distraction instrument for treating injuries and diseases of bones and joints, comprising: needles that can be passed through affected bone fragments of a limb to be joined; ring frame means having attachments for immobilizing said needles; longitudinal members interconnecting said ring frame means to form a single frame system about the affected limb; at least one of said ring frame means being formed as a set of two concentric, spaced-apart rings, substantially in the same plane, namely an inner ring and an outer one, capable of withstanding lateral, rotary and angular tensional forces, said inner ring carrying said needles and rods that radially protrude therefrom, said rods being also fastened to said outer ring, while the latter is connected with said longitudinal members, and load-bearing threaded attachments for fastening said rods to said outer ring at any point along said rods as well as over a selected section along the circumference of said outer ring, so that said inner ring, and hence the affected bone fragments, can be set to any desired position within said outer ring.

2. A surgical compression-distraction instrument for treating injuries and diseases of bones and joints, comprising: needles that can be passed through affected bone fragments of a limb to be joined; ring frame means having attachments for immobilizing said needles; longitudinal members interconnecting said ring frame means to form a single frame system about the affected limb; at least one of said ring frame means being formed as a set of two concentric, spaced-apart rings, substantially in the same plane, namely an inner ring and an outer one, said inner ring carrying said needles and rods that radially protrude therefrom, said rods being also fastened to said outer ring, while the latter is connected with said longitudinal members, and load-bearing threaded attachments for fastening said rods to said outer ring at any point along said rods as well as over a selected section along the circumference of said outer ring, so that said inner ring, and hence the affected bone fragments, can be set to any desired position within said outer ring, wherein the latter includes two parallel rings mounted with the aid of spacers with a certain clearance therebetween, and said rods of the inner ring are formed as threaded studs which can be displaced in said clearance in the course of adjustments and are secured to said outer ring in predetermined positions with the aid of nuts.

3. The surgical instrument as defined in claim 2, wherein said inner ring has a diameter 1.5 times smaller than that of said two parallel rings of the outer ring.

4. A surgical compression-distraction instrument for treating injuries and diseases of bones and joints, comprising: needles that can be passed through affected bone fragments of a limb to be joined; ring frame means having attachments for immobilizing said needles; longitudinal members interconnecting said ring frame means to form a single frame system about the affected limb; at least one of said ring frame means being formed as a set of two concentric, spaced-apart rings, substantially in the same plane, namely an inner ring and an outer one, said inner ring carrying said needles and rods that radially protrude therefrom, said rods being also fastened to said outer ring, while the latter is connected with said longitudinal members, and load-bearing threaded attachments for fastening said rods to said outer ring at any point along said rods as well as over a selected section along the circumference of said outer ring, so that said inner ring, and hence the affected bone fragments, can be set to any desired position within said outer ring, wherein the latter and the ends of said rods of the inner ring being provided with spacers having thereon eyes that can receive screw distance stays fixable to said inner ring by nuts in any desired position, so that said inner ring can be positioned in a plane turned by an angle relative to that of said outer ring.

* * * * *